United States Patent [19]

Valange

[11] Patent Number: 4,460,406
[45] Date of Patent: Jul. 17, 1984

[54] HERBICIDAL CONCENTRATED EMULSIONS

[75] Inventor: Baudouin M. Valange, Creve Coeur, Mo.

[73] Assignee: Monsanto Company, St. Louis, Mo.

[21] Appl. No.: 369,697

[22] Filed: Apr. 19, 1982

[51] Int. Cl.³ ............................................. A01N 25/02
[52] U.S. Cl. ...................................... 71/100; 71/118; 71/DIG. 1
[58] Field of Search ................... 71/DIG. 1, 100, 118

[56] References Cited

U.S. PATENT DOCUMENTS 4,174,960 11/1979 Hendriksen ......................... 71/121
4,182,699 1/1980 Fan ..................................... 260/29.6

FOREIGN PATENT DOCUMENTS 2048675 12/1980 United Kingdom .

*Primary Examiner*—Catherine L. Mills
*Attorney, Agent, or Firm*—Patricia A. Coburn; Howard C. Stanley

[57] ABSTRACT

The invention is directed to a herbicidal composition which is a concentrated, oil/water emulsion formulation (CE). The concentrated emulsion formulations of the invention are particularly useful for formulating herbicidal agents which have a solution point in solvent at around 25° C. or less, particularly 2-chloro-2',6'-diethyl-N-(methoxymethyl)acetanilide, N-(ethoxymethyl)-2'-trifluoromethyl-6'-methyl-2-chloroacetanilide and S-2,3,3-trichloroallyl diisopropyl thiocarbamate. The concentrated oil/water emulsion formulations of the present invention are comprised of the following components:

| Component | % By Weight |
|---|---|
| Active Herbicidal Agent | 40–65 |
| Hydrocarbon solvent | 15–30 |
| Emulsifier | 2.5–10 |
| Co-Emulsifier | 0.5–5 |
| Water (4–20% Agriculturally Acceptable Salt) | Balance |
| Total | 100.00 |

9 Claims, No Drawings

4,460,406

HERBICIDAL CONCENTRATED EMULSIONS

BACKGROUND OF THE INVENTION

The invention relates to herbicidal formulations in the form of a concentrated oil-in-water emulsion (CE) containing concentrated amounts of certain herbicidal compounds which are solid at room temperature and which have a solution point in solvent at around 25° C. or less.

A concentrated emulsion formulation consists of two phases, and is a dispersion of one immiscible liquid in a second called the continuous phase. If the continuous phase is water, the emulsion is an oil in water (O/W) emulsion. The concentrated emulsion formulations of this invention are oil/water emulsions.

Many herbicidally active materials, as for example, 2-chloro-2',6'-diethyl-N-(methoxymethyl) acetanilide (commonly known as alachlor), sold under the trade name LASSO ®, are available as emulsifiable concentrate (EC) formulations. An emulsifiable concentrate is a formulation in which the active ingredient is dissolved in an organic solvent along with added emulsifiers or dispersants. When the concentrate is added to water, the active ingredient becomes dispersed throughout the water.

Emulsifiable concentrate formulations are generally effective, in that one is able to produce a formulation containing concentrated amounts of active material (e.g., 4 lb/gal), which is readily dispersible in large volumes of water in preparation for spraying and is capable of undergoing temperature fluctuations. However, since an emulsifiable concentrate formulation consists mainly of the active agent plus organic solvent, such formulations suffer from the disadvantage that bulk storage carries potential environmental and/or health hazards, risk of fire associated with storage of organic solvents, plus the commercial penalty of the high cost of organic solvents. Accordingly, it is highly desirable to formulate herbicidal actives such as, e.g., alachlor, in such a fashion as to reduce the amount of organic solvent used in the formulation and to produce a formulation with a good stability over a broad range of storage temperatures, including an ability to retain the formulation integrity after being frozen.

An advantage of the concentrated emulsion compositions of the present invention, when compared to an emulsifiable concentrate composition, is that the amount of organic solvent normally used is replaced by water; concentrated emulsion formulations are thus less irritating to the eye, quantity of solvent evaporated to the environment is reduced and the formulations are less expensive. The present concentrated emulsions require about less than half the amount of organic solvent as conventional emulsifiable concentrate formulations. The concentrated emulsion formulations of the present invention have been found to disperse readily when added to large volumes of water. Such dispersions are readily applied to crop land by conventional agricultural spraying means and, as would be recognized by one skilled in the art, they are applied in a similar manner to the known emulsifiable concentrate formulations.

Because herbicide formulations are often stored for long periods of time under changing temperature conditions, it is necessary that such formulations have a stability over a broad range of storage temperatures, including an ability to retain formulation integrity after being frozen. While preformed emulsions of lipophilic substances in aqueous media are known, mainly in the cosmetic, food and pharmaceutical industries, these emulsions are incapable of undergoing repeated freeze/thaw conditions without the emulsion breaking or formation of crystals of active agent at cold temperatures.

Pesticide formulations which are oil/water emulsions are known in the art, for example, Great Britain Pat. No. 2,048,675 and U.S. Pat. No. 4,174,960. This latter patent describes a concentrated emulsion formulation of trifluralin herbicide. When the cold temperature stability of the formulations of this invention is compared to the prior art formulation, unexpectedly superior cold temperature stability is observed with the formulations of this invention. It is, accordingly, a particular object of this invention to afford an oil-in-water emulsion formulation of certain herbicides, especially alachlor, wherein the emulsion exhibits excellent high and low temperature stability and wherein the disadvantage of emulsifiable concentrate formulations, that is, the presence of large amounts of organic solvent, is minimized.

DETAILED DESCRIPTION OF THE INVENTION

The present invention is directed to a concentrated, oil-in-water emulsion formulation of certain herbicides which have a solution point in solvent at around 25° C. or less. The concentrated oil/water emulsion formulations of the present invention are comprised of the following components:

| Components | % By Weight |
| --- | --- |
| Active Herbicidal Agent | 40–65 |
| Hydrocarbon solvent | 15–30 |
| Emulsifier | 2.5–10 |
| Co-Emulsifier | 0.5–5 |
| Water (4.0–20.0% Agriculturally Acceptable Salt) | Balance |
| Total | 100.00 |

The term "Active Herbicidal Agent" as used herein refers to pesticidally active compounds which are solid at room temperature and which have a solution point in solvent at around 25° C. or less. Preferred for use herein are 2-haloacetanilide and thiocarbamate herbicides. Specifically contemplated for use in the present invention are the following herbicidally active compounds: 2-chloro-2',6'-diethyl-N-(methoxymethyl)acetanilide (commonly known as alachlor); N-(ethoxymethyl)-2'-trifluoromethyl-6'-methyl-2-chloroacetanilide; S-2,3,3-trichloroallyl diisopropylthiocarbamate (commonly known as triallate) and S-2,3-dichloroallyl diisopropylthiocarbamate (commonly known as diallate).

The preparation and herbicidal use of alachlor, is described in U.S. Pat. Nos. 3,442,945 and 3,547,620. The preparation and herbicidal use of N-ethoxymethyl-2'-trifluoromethyl-6'-methyl-2-chloroacetanilide is described in Belgium Pat. No. 887,997. The preparation of the thiocarbamate herbicides is described in U.S. Pat. No. 3,330,821 and their herbicidal use is described in U.S. Pat. No. 3,330,643.

As used herein the term "solution point" is understood to mean the following: the temperature at which a given composition of a particular active and solvent is a saturated solution; or stated another way, the temperature at which, for a given composition of a particular active and solvent, fine crystals formed by cooling below that temperature, dissolve.

As used herein the term "hydrocarbon solvent" refers to a single organic solvent or may refer to a blend of two or more such materials. The hydrocarbon solvent useful herein is one in which the herbicidal material readily dissolves and which is substantially immiscible with water. Examples of suitable solvents include aromatic hydrocarbons, such as xylene, trimethylbenzene, polynuclear aromatic hydrocarbons such as naphthalene and alkyl naphthalenes, halogenated aromatic hydrocarbons such as monochlorobenzene, o-chlorotoluene and the like.

The emulsifying agent used herein may consist of a single emulsifying agent or may be a blend of emulsifying agents and may be a nonionic, anionic or cationic surfactant or a blend of two or more such surfactants; preferred for use herein are nonionic and anionic emulsifiers. Such surface-active agents are described in McCUTCHEON'S DETERGENTS AND EMULSIFIERS, North American Edition, 1980 Annual published by the McCutcheon Division, MC Publishing Company, 175 Rock Road, Glen Rock, N.J. 07452, USA.

Especially suitable nonionic emulsifying agents are those with a hydrophile-lipophile balance (HLB) of 16.0 or greater as determined by the method described by Paul L. Lindner in EMULSIONS AND EMULSION TECHNOLOGY, edited by Kenneth Lissant, published by Dekker, New York, N.Y., 1974, pages 188–190. Preferred for use herein are the nonionic surfactants having an HLB of 18.0 or greater, most preferably those nonionics having an HLB of 18.0–20.0.

Exemplary of such nonionic emulsifiers are "BRIJ 78", the trade name for a polyoxyethylene (20) stearyl alcohol having an HLB of 15.3; "BRIJ 700", the trade name for a polyoxyethylene (100) stearyl alcohol having an HLB of 18.8; "MYRJ 53", a polyoxyethylene (50) stearate with an HLB of 17.9, "MYRJ 59", a polyoxyethylene stearate (100) having an HLB of 18.8; "Renex 650", the trade name of a polyoxyethylene (30) nonylphenol having an HLB of 17.1; and "Atlox" G7596HJ and G1300, respectively an ethoxylated sorbitan ester having an HLB of 19.1 and a polyoxyethylene fatty glyceride having an HLB of 18.1. All of these materials are available from ICI Americas, Inc., New Murphy Road and Concord Pike, Wilmington, Del. USA 19897.

Other suitable nonionic emulsifiers are nonylphenol ethoxylate, as for example, "Cedopol CO 990" having an HLB of 19.0 and available from Domtar Inc./CDC Division, 1136 Matheson Boulevard, Mississauga, Ontario Canada L4W2V4 and "Gafac" CO 990 available from GAF Corporation, Chemical Products, 140 W. 51st Street, New York, N.Y., USA, 10020.

Suitable anionic emulsifiers found to be useful herein are, for example, the sodium alkylaryl sulfates, available under the trade name "Witcolate" D51-52, D51-53 and D-51-51 manufactured by the Witco Chemical Corporation, Organics Division, 77 Park Avenue, New York, N.Y., USA, 10017. Certain anionic/nonionic formulated blends, as for example, "Atlox" 4861B available from ICI Americas are also useful for use in the present invention.

As used herein, the term "co-emulsifier" refers to a straight chain alcohol having a carbon content of $C_{12-20}$, preferably $C_{14-18}$; such alcohols are: 1-dodecanol, 1-tridecanol, 1-tetradecanol, 1-pentadecanol, 1-hexadecanol, 1-heptadecanol, 1-octadecanol, 1-nonadecanol and 1-eicosanol. The co-emulsifier is not, by itself, a surface active agent; however, in the presence of the emulsifier used in the formulation of this invention, the co-emulsifier is found at the oil/water interface and modifies the properties of the emulsifier.

The balance of the composition described herein is made up of water containing an agriculturally acceptable salt or urea to increase the specific gravity of the water and/or depress the freezing point of the aqueous phase. As would be recognized by one skilled in this art, any inorganic or organic salt which is compatible with the agricultural chemical formulations of this invention may be utilized herein to alter the specific gravity of the water used in the emulsion formulations of the invention. Salts which have been found to be useful herein include sodium chloride, potassium chloride, ammonium chloride, calcium chloride, magnesium chloride, ammonium nitrate, ammonium carbonate, magnesium oxide and the like.

Minor quantities, i.e., from about 0.5 to about 5.0% by weight of total composition, of one or more inert formulation adjuvants, such as anti-foaming agents, anti-caking agents, biocides, dyes, anti-corrosion agents, freeze-depressants and the like may be incorporated into the concentrated emulsion compositions of the present invention, especially if said compositions are to be stored for any extended period of time prior to use, particularly under adverse storage conditions.

In general, the active herbicidal ingredient will be present in the concentrated emulsion formulation of this invention at a concentration of from about 40.0 to about 65.0% by weight, preferably at a concentration of from about 40.0 to about 50.0% by weight and most preferably at about 42.0 to about 45.0% by weight of total composition. The concentration of the hydrocarbon solvent present in the formulation will range from about 15.0 to about 30.0% by weight, preferably about 17.5 to about 25.0% by weight, more preferably at about 18.0 to about 22.0% by weight of total composition. The concentration of the emulsifier will range from about 3.0 to about 10.0% by weight, preferably about 2.0 to about 7.0% by weight and more preferably about 3% by weight of total composition. The co-emulsifier will be present in the formulation at about 0.2 to about 5.0% by weight, preferably at about 0.5 to about 1.5% by weight of total composition.

Water forms the balance of the emulsion formulation of the invention and will contain a salt(s) dissolved therein at a concentration of from about 4.0 to about 20.0% by weight of the water present in the formulation, preferably from about 4.0 to about 17.5% by weight of the water and more preferably, about 10.0 to about 15.0% by weight of the water present in the composition. The water containing the dissolved salt forms the continuous phase and is herein referred to as the "continuous phase liquid".

It has been found that the order of addition of the components of the concentrated emulsion compositions described herein will affect the quality of the emulsion formed. Accordingly, it is preferred that the concentrated herbicidal emulsions of the present invention be prepared according to the following steps:

(1) The organic solvent, herbicidal active ingredient emulsifier and the co-emulsifier are dissolved together to form the discontinuous, i.e., organic phase liquid; it may be necessary to add heat sufficient to dissolve the emulsifier(s) and/or co-emulsifier;

(2) The salt, e.g., NaCl is dissolved in the water to form the continuous phase liquid, i.e., the aqueous phase liquid;

(3) The discontinuous phase liquid of Step 1 is added to the continuous phase of Step 2, utilizing high shear to form an oil-in-water emulsion.

Any shearing means known to those in the art to be capable of producing sufficient shear to produce dispersion, emulsification and/or homogenization is suitable for use herein. Illustrative of such shearing means is the "Polytron" homogenizer, sold by Brinkmann Instruments, Inc., Cantiague Road, Westbury, N.Y. 11590, USA, which utilizes mechanical shearing with sonic energy to effect homogenization, dispersion or emulsification and the Tekmar, "Dispax Reactor DR 3-916", available from the Tekmar Company, P. O. Box 372021, Cincinnati, Ohio 45222, USA.

Generally speaking, the mean droplet diameter of the discontinuous phase, that is, the organic phase liquid observed throughout the continuous phase will range from about 0.2 to about 10.0 microns; the average size will range from about 2.0 to about 3.0 microns.

The following examples are illustrative of the concentrated emulsion compositions contemplated by the present invention. Unless otherwise indicated, all examples were prepared according to the procedure described in Example 1.

EXAMPLE 1

This example illustrates several of the concentrated emulsion (CE) formulations of the present invention, as well as the superior cold temperature stability of the formulations. The CE's of this example were prepared as follows: alachlor, emulsifier and co-emulsifier (1-tetradecanol [C140H], 1-hexadecanol [C160H] and 1-octadecanol [C180H]) were dissolved in monochlorobenzene (MCB) with gentle warming to 55° C. The aqueous solution containing calcium chloride at a concentration of 5.0% by weight of the water was separately prepared at room temperature. The organic phase liquid was added to the aqueous solution with strong agitation. The resulting emulsion was opaque and white in color (a dye may be optionally used to impart desired color to the emulsion).

The cold stability tests were conducted as follows:

(1) The emulsion formulation was cooled to 0° C.; an alachlor crystal was added to the concentrated emulsion (CE) and the CE was stored for 2 weeks at −9° C.; at the end of this period the formulation was sieved on 50 mesh screen to determine whether there were any herbicide crystals present other than the original seed;

(2) The formulation from Step 1 was diluted with water (5:95 dilution) and the diluted emulsion cooled to 0° C.; an alachlor crystal was added to the diluted formulation and the diluted emulsion was stored for 3 days (72 hours) at 0° C.; at the end of this period the diluted formulation was sieved on 50 mesh screen to determine whether there were any herbicide crystals present in the diluted formulation other than the original seed.

TABLE I

| | | Composition of Dispersed (Organic Phase)* % By Weight of Total Formulation | | | | | | | |
|---|---|---|---|---|---|---|---|---|---|
| | | Co-emulsifier | | | Emulsifier | | Dilution Test 0° C. | | Concentrated Form −9° C. |
| Alachlor | MCB | C140H | C160H | C180H | Atlox G7596HJ | Witcolate D5151 | 24 hr | 72 hr | 2 wks. |
| 42.8 | 20.0 | 0.7 | 2.0 | 0.2 | 3.0 | 0.5 | 0 | trace | + |
| 42.8 | 21.3 | 0.2 | 1.70 | 0.6 | 3.0 | — | trace | + | trace |
| 42.8 | 20.0 | 0.7 | 2.0 | 0.2 | 3.0 | 0.6 | 0 | ++ | + |
| 42.8 | 20.0 | 0.3 | 2.7 | 1.0 | 2.5 | — | 0 | 0 | 0 |
| 42.8 | 20.0 | 0.7 | 2.0 | 0.2 | 2.5 | 1.0 | trace | + | + |
| 42.8 | 20.0 | 0.5 | 2.0 | 0.5 | 2.5 | 1.0 | trace | + | + |
| 42.8 | 20.0 | 0.3 | 2.4 | 0.8 | 2.6 | — | 0 | 0 | 0 |

Crystals Retained on 50 Mesh Screen
0 - None
+ - <1%
++ - 5-10%
*In each of the above formulations, the aqueous (continuous) phase formed the balance of the formulation to bring the total to 100%; the water contained 15% by weight of said water of CaCl$_2$.

In accordance with the procedure described in Example 1, the following examples may be prepared.

EXAMPLE 2

| Component | % By Weight |
|---|---|
| Triallate | 43.71 |
| Heavy Aromatic Naphtha | 17.00 |
| Emulsifier | |
| Renex 650 | 2.55 |
| Atlox 4861B | 0.45 |
| Ethylene glycol | 4.50 |
| Water (4.3% CaCl$_2$) | Balance |
| Total | 100.00 |

EXAMPLE 3

| Component | % By Weight |
|---|---|
| Triallate | 42.4 |
| Xylene | 19.6 |
| Emulsifier | |
| BRIJ 700 | 1.5 |
| MYRJ 59 | 1.5 |
| 1-Octadecanol | 1.0 |
| Water (5.2% NaCl) | Balance |
| Total | 100.00 |

EXAMPLE 4

| Component | % By Weight |
|---|---|
| Triallate | 42.4 |
| Xylene | 19.6 |
| Emulsifier | |

-continued

| Component | % By Weight |
| --- | --- |
| BRIJ 78 | 1.5 |
| BRIJ 700 | 1.5 |
| 1-Octadecanol | 1.0 |
| Water (5.1% CaCl$_2$) | Balance |
| Total | 100.00 |

EXAMPLE 5

| Component | % By Weight |
| --- | --- |
| Alachlor | 45.0 |
| Monochlorobenzene | 19.5 |
| Emulsifier | |
| BRIJ 78* | 1.5 |
| BRIJ 700** | 1.5 |
| Anti-foam Agent | 0.02 |
| Dye (Methyl Violet) | 0.01 |
| 1-Octadecanol | 1.0 |
| Water (4.7% CaCl$_2$) | Balance |
| Total | 100.00 |

EXAMPLE 6

| Component | % By Weight |
| --- | --- |
| N—(ethoxymethyl)-2'-trifluoromethyl-6'-methyl-2-chloroacetanilide | 43.70 |
| Xylene | 18.00 |
| C$_9$ Aromatic | 4.00 |
| Emulsifier | |
| Atlox G7596HJ | 2.30 |
| GAFAC CO 990 | 1.00 |
| Co-emulsifier | |
| C14OH | 0.3 |
| C16OH | 2.0 |
| C18OH | 0.7 |
| Water (4.2% CaCl$_2$) | Balance |
| Total | 100.00 |

EXAMPLE 7

| Component | % By Weight |
| --- | --- |
| Alachlor | 42.78 |
| Monochlorobenzene | 20.0 |
| Emulsifier | |
| Atlox G7596HJ | 2.4 |
| Witcolate D51-51 | 1.5 |
| 1-Hexadecanol | 2.8 |
| Anti-foam Agent | 0.02 |
| Water (15% CaCl$_2$) | Balance |
| Total | 100.00 |

EXAMPLE 8

| Component | % By Weight |
| --- | --- |
| N—(ethoxymethyl)-2'-trifluoromethyl-6'-methyl-2-chloroacetanilide | 44.7 |
| Xylene | 18.0 |
| Emulsifier | |
| BRIJ 78 | 1.6 |
| BRIJ 700 | 1.4 |
| 1-Octadecanol | 1.0 |
| Anti-foam Agent | 0.02 |
| Water (15% CaCl$_2$) | Balance |
| Total | 100.00 |

The following example illustrates the herbicidal efficacy of the present concentrated emulsion herbicide formulations.

EXAMPLE 9

Foxtail and barnyardgrass were planted in four inch pots, with four replications per treatment and the pots were thereafter treated with varying rates of herbicidal material as shown in Table II. Pots treated with no herbicide served as controls. Treatments were applied with a belt sprayer using a spray volume of 20 GPA at 30 PSI. The pots received ¼ inch overhead irrigation following treatment (including controls). Visual estimates for percent control were made nine days after treatment. The results are summarized in Table II.

TABLE II

| Treatment | Rate (lb/acre) | BYDG* % Control | FXTL** % Control |
| --- | --- | --- | --- |
| Lasso ® EC*** | 1/64 | 5.25 | 58.8 |
| | 1/32 | 80.00 | 71.2 |
| | 1/16 | 91.2 | 93.8 |
| | 1/8 | 99.0 | 98.8 |
| Concentrated | 1/64 | 55.0 | 58.8 |
| Emulsion of | 1/32 | 82.5 | 80.0 |
| Example 7 | 1/16 | 92.5 | 90.0 |
| | 1/8 | 97.0 | 98.2 |

*BYDG — Barnyardgrass
**FXTL — Foxtail
***Lasso ® EC — emulsifiable concentrate formulation containing 4 pounds/gallon alachlor as active ingredient.

It is to be understood that although the invention has been described with specific reference to particular embodiments thereof, it is not to be so limited, since changes and alterations therein may be made which are within the full intended scope of this invention as defined by the appended claims.

I claim:

1. A herbicidal concentrated emulsion composition consisting essentially of the following components:

A. from about 40.0 to about 65.0 percent by weight of a 2-haloacetanilide or thiocarbamate herbicide which is a solid at room temperature and which has a solution point in water of about 25° C. or less;

B. from about 15.0 to about 30.0 percent by weight of a hydrocarbon solvent;

C. from about 2.5 to about 10.0 percent by weight of an emulsifier which is a nonionic emulsifying agent having an HLB of 18.0 or greater;

D. from about 0.5 to about 5.0 percent by weight of a C$_{14-20}$ straight chain alcohol; and E. balance being made up of water containing an agriculturally acceptable salt or urea at a concentration of from about 4.0 to about 20.0 percent by weight of the water.

2. An emulsion composition according to claim 1 wherein said herbicide is selected from the group consisting of 2-chloro-2',6'-diethyl-N-(methoxymethyl)-acetanilide, N-(ethoxymethyl)-2'-trifluoromethyl-6'-methyl-2-chloroacetanilide, S-2,3,3-trichloroallyl diisopropylthiocarbamate and S-2,3-dichloroallyl diisopropylthiocarbamate.

3. An emulsion composition according to claim 1 wherein the concentration of said herbicide is from 40.0 to 50.0% by weight of total composition; wherein the concentration of said hydrocarbon solvent is from 17.5 to 25.0% by weight of total composition; wherein the concentration of said emulsifier is from 2.0 to 7.0% by weight of total composition; and wherein the concentration of said co-emulsifier is from 0.5 to 1.5% by weight of total composition.

4. An emulsion composition according to claim 3 wherein the concentration of said herbicide is from 42.0 to 45.0% by weight of total composition; wherein the concentration of said hydrocarbon solvent is from 18.0 to 22.0% by weight of total composition; and wherein the composition of said emulsifier is 2.0–3.8% by weight of total composition.

5. An emulsion composition according to claim 3 wherein the concentration of said agriculturally acceptable salt or urea is 4.0 to 15.0% by weight of the water present in the composition.

6. An emulsion composition according to claim 5 wherein said inorganic salt is selected from the group consisting of sodium chloride, calcium chloride, potassium chloride, magnesium chloride and magnesium oxide.

7. An emulsion composition according to claim 2 wherein said hydrocarbon solvent is selected from the group consisting of monochlorobenzene, xylene, $C_9$ aromatic and heavy aromatic naphtha.

8. An emulsion composition according to claim 1 wherein said emulsifier is a sodium alkylaryl sulfate anionic emulsifying agent.

9. An emulsion composition according to claim 1 containing from about 0.5 to about 5.0 percent of inert formulation adjuvants.

* * * * *